(12) United States Patent
Biedermann (10) Patent No.: US 12,082,859 B2
(45) Date of Patent: Sep. 10, 2024

(54) SYSTEM OF A BONE ANCHOR AND AN ELONGATE INSTRUMENT

(71) Applicant: BIEDERMANN TECHNOLOGIES GMBH & CO. KG, Donaueschingen (DE)

(72) Inventor: Timo Biedermann, Trossingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 244 days.

(21) Appl. No.: 17/521,418

(22) Filed: Nov. 8, 2021

(65) Prior Publication Data
US 2022/0133374 A1 May 5, 2022

Related U.S. Application Data

(63) Continuation of application No. 16/270,029, filed on Feb. 7, 2019, now Pat. No. 11,191,583.
(Continued)

(30) Foreign Application Priority Data

Feb. 9, 2018 (EP) .................................... 18156123

(51) Int. Cl.
*A61B 17/86* (2006.01)
*A61B 17/16* (2006.01)
(Continued)

(52) U.S. Cl.
CPC ........ *A61B 17/864* (2013.01); *A61B 17/1615* (2013.01); *A61B 17/1725* (2013.01);
(Continued)

(58) Field of Classification Search
CPC ....... A61B 17/86; A61B 17/88; A61B 17/864; A61B 17/8897; A61B 17/16; A61B 17/1615; A61B 17/17; A61B 17/1725
See application file for complete search history.

(56) References Cited

U.S. PATENT DOCUMENTS

| 5,098,435 A * | 3/1992 | Stednitz | A61B 17/1637 606/907 |
| 5,209,753 A | 5/1993 | Biedermann et al. | |

(Continued)

FOREIGN PATENT DOCUMENTS

| EP | 3 210 554 A1 | 8/2017 |
| WO | 2016/100570 A1 | 6/2016 |
| WO | WO 2017/147537 A1 | 8/2017 |

OTHER PUBLICATIONS

Extended European Search Report for Application No. 18156123.4, mailed Jul. 23, 2018, 7 pages.

*Primary Examiner* — Christopher J Beccia
(74) *Attorney, Agent, or Firm* — Lewis Roca Rothgerber Christie LLP (57) ABSTRACT

A system includes a bone anchor including a shank having a first end, a second end, a channel extending through the shank with a channel axis, and an internal advancement structure having at least a portion being closer axially to the second end than to the first end, and an elongate instrument configured to extend through the channel, with a tip portion and an external advancement structure configured to cooperate with the internal advancement structure. Engagement between the advancement structures facilitates holding of the tip portion at a first axial position relative to the bone anchor and movement of the tip portion from the first axial position towards both the first and second ends of the shank. The tip portion and the external advancement structure of (Continued)

the elongate instrument are insertable into and removable from the channel via the first end of the shank.

20 Claims, 5 Drawing Sheets

Related U.S. Application Data (60) Provisional application No. 62/628,820, filed on Feb. 9, 2018.

(51) Int. Cl.
*A61B 17/17* (2006.01)
*A61B 17/88* (2006.01)
*A61B 90/00* (2016.01)
*A61B 17/56* (2006.01)

(52) U.S. Cl.
CPC ...... *A61B 17/8811* (2013.01); *A61B 17/8875* (2013.01); *A61B 17/8897* (2013.01); *A61B 90/39* (2016.02); *A61B 2017/564* (2013.01); *A61B 2090/3966* (2016.02)

(56) References Cited

U.S. PATENT DOCUMENTS

| 5,957,953 | A  | * | 9/1999 | DiPoto | A61B 17/0401 |
|---|---|---|---|---|---|
| | | | | | 606/313 |
| 7,938,848 | B2 | | 5/2011 | Sweeney | |
| 8,690,930 | B2 | | 4/2014 | Biedermann et al. | |
| 9,095,395 | B2 | | 8/2015 | Beger et al. | |
| 11,191,583 | B2 | * | 12/2021 | Biedermann | A61B 90/39 |
| 2009/0112270 | A1 | * | 4/2009 | Lunn | A61B 17/0401 |
| | | | | | 606/301 |
| 2009/0149862 | A1 | * | 6/2009 | Kim | A61B 90/39 |
| | | | | | 606/104 |
| 2009/0187220 | A1 | | 7/2009 | Hamada | |
| 2009/0275994 | A1 | | 11/2009 | Phan et al. | |
| 2010/0280558 | A1 | | 11/2010 | Biyani et al. | |
| 2016/0374740 | A1 | | 12/2016 | Donald | |

* cited by examiner

SYSTEM OF A BONE ANCHOR AND AN ELONGATE INSTRUMENT

CROSS-REFERENCE TO RELATED APPLICATION(S)

This application is a continuation of U.S. patent application Ser. No. 16/270,029, filed Feb. 7, 2019, which claims priority to and the benefit of U.S. Provisional Patent Application No. 62/628,820, filed Feb. 9, 2018, the contents of which are hereby incorporated by reference in their entirety, and claims priority from European Patent Application EP 18 156 123.4, filed Feb. 9, 2018, the contents of which are hereby incorporated by reference in their entirety.

BACKGROUND

The application relates to a system including a bone anchor with a cannulated shank and an elongate instrument that is insertable into the cannulated shank.

DESCRIPTION OF RELATED ART

In procedures of spinal surgery, in particular minimally invasive surgery (MIS), a guide wire, such as a Kirschner wire (K-wire), can be placed percutaneously through the skin to an intended position of a bone anchor in a vertebra of a patient's vertebral column. In some cases, a hole for the bone anchor is pre-drilled and a thread for the bone anchor is pre-tapped. The bone anchor, which has a cannulated shank, is then guided along the guide wire and finally screwed into, for example, a pedicle of the vertebra. Thereafter, the guide wire is removed. Such a bone anchor and procedure is known, for example, from U.S. Pat. No. 8,690,930 B2.

Other bone anchors are cannulated for guiding through a guide pin or a drill. For example, U.S. Pat. No. 5,098,435 describes a bone stabilizing system including a guide pin and a cannula forming a bone anchor, wherein the guide pin is provided with a drilling means at a forward end thereof for drilling a guide hole into a fractured bone at a predetermined location. The use of the system includes the steps of inserting the guide pin into bone, placing the cannula over the guide pin, and advance the cannula into the bone.

U.S. Pat. No. 7,938,848 B2 describes a pedicle screw having a channel extending along a longitudinal axis of the screw. A drill extends through the channel, wherein a first end of the drill extends out of the distal opening of the channel.

U.S. Pat. No. 9,095,395 B2 describes a surgical K-wire for guiding a bone screw comprising a longitudinal channel, wherein a closure element is formed at a distal end of the K-wire for closing-off the distal end outlet opening of the longitudinal channel of the bone screw. In some embodiments, the closure element is connected to the longitudinal channel by threads.

SUMMARY

It is an object of the invention to provide a system including a bone anchor and an elongate instrument which has a broad range of applications and which simplifies surgical procedures, in particular, MIS-procedures.

The elongate instrument of the system may be, for example, a cutting device, a K-wire, a sensor for sensing characteristics at the implantation site, or a marker or any other instrument. Each elongate instrument and the bone anchor together form a unit that can be placed on the implantation site, and the surgical step associated with the elongate instrument can be carried out. After that, the instrument can be removed from the channel of the bone anchor, and if necessary, another type of elongate instrument may be inserted into the channel. Hence, the bone anchor can be assembled selectively with various instruments, according to the specific function needed. This provides a broad range of applications for the system.

In the case of the elongate instrument being a cutting device, the system permits placing of the bone anchor with the inserted cutting device without using a K-wire, pre-drilling a hole, or pre-tapping a thread. This saves time in a surgical procedure. Moreover, a cutting device with a shape and a length of the cutting portion suitable for the specific clinical situation in which the bone anchor is to be used, can be selected.

In the case of the elongate instrument being a K-wire, the system permits placing of the bone anchor with the K-wire as a unit onto the bone surface and pressing the K-wire tip into the bone. Thereafter, the K-wire can be used as a guiding means.

In the case of the elongate instrument being a marker, the bone anchor and a marker element may have a defined positional relationship relative to each other, such that a position of the bone anchor may be precisely detected.

BRIEF DESCRIPTION OF THE DRAWINGS

Further features and advantages will become apparent from the description of embodiments of the invention by means of the accompanying drawings. In the drawings:

FIG. 3b shows an enlarged portion of FIG. 3a.

FIG. 4 shows a perspective view of an instrument attached to the system of FIGS. 1 to 3b during a step of implanting the bone anchor into a pedicle of a vertebra.

DETAILED DESCRIPTION

FIGS. 1 to 4 show an embodiment of a system including a bone anchor 1 and an elongate instrument, for example, in the form of a cutting device 20. The bone anchor 1 includes a shank 2 with a head 3 at a first end and a free second end 4. The head 3 may have a spherically shaped outer surface portion that defines a largest outer diameter of the bone anchor 1. A bone thread 5 may be provided on at least a portion of the outer surface of the shank 2. The shank 2 may slightly taper and narrow towards the second end 4. An engagement recess 6 for engagement with a tool, may be formed at a free end surface of the head 3.

Figure 1:
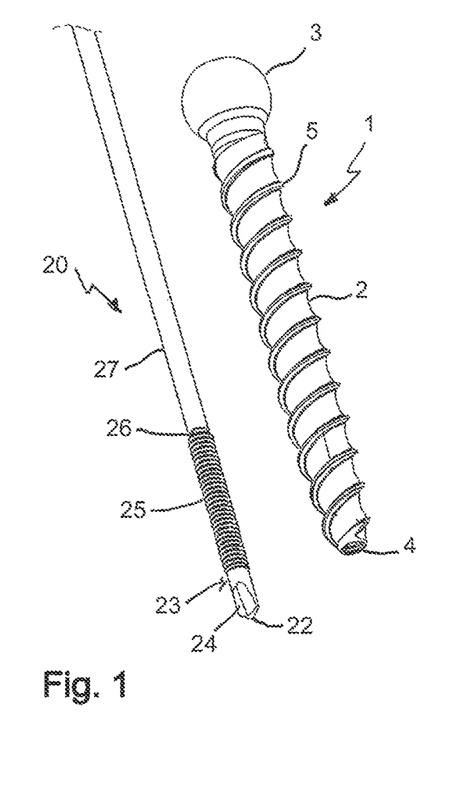
FIG. 1 shows a perspective exploded view of an embodiment of a system including a bone anchor and an elongate instrument in the form of a cutting device.
Figure 2:
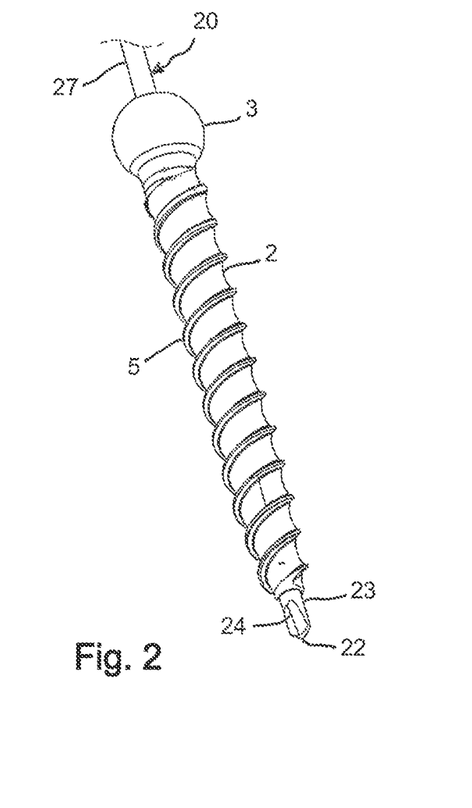
FIG. 2 shows a perspective view of the system of FIG. 1 in an assembled state.
Figure 3A:
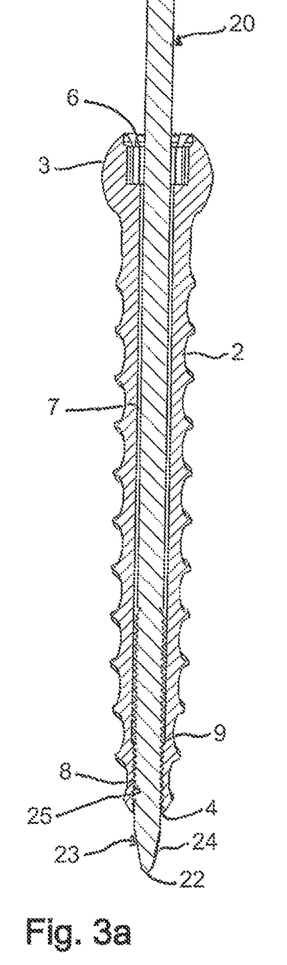
FIG. 3a shows a cross-sectional view of the system of FIGS. 1 and 2, the cross-section taken in a plane extending through a channel axis of the bone anchor.
Figures 3B, 4:
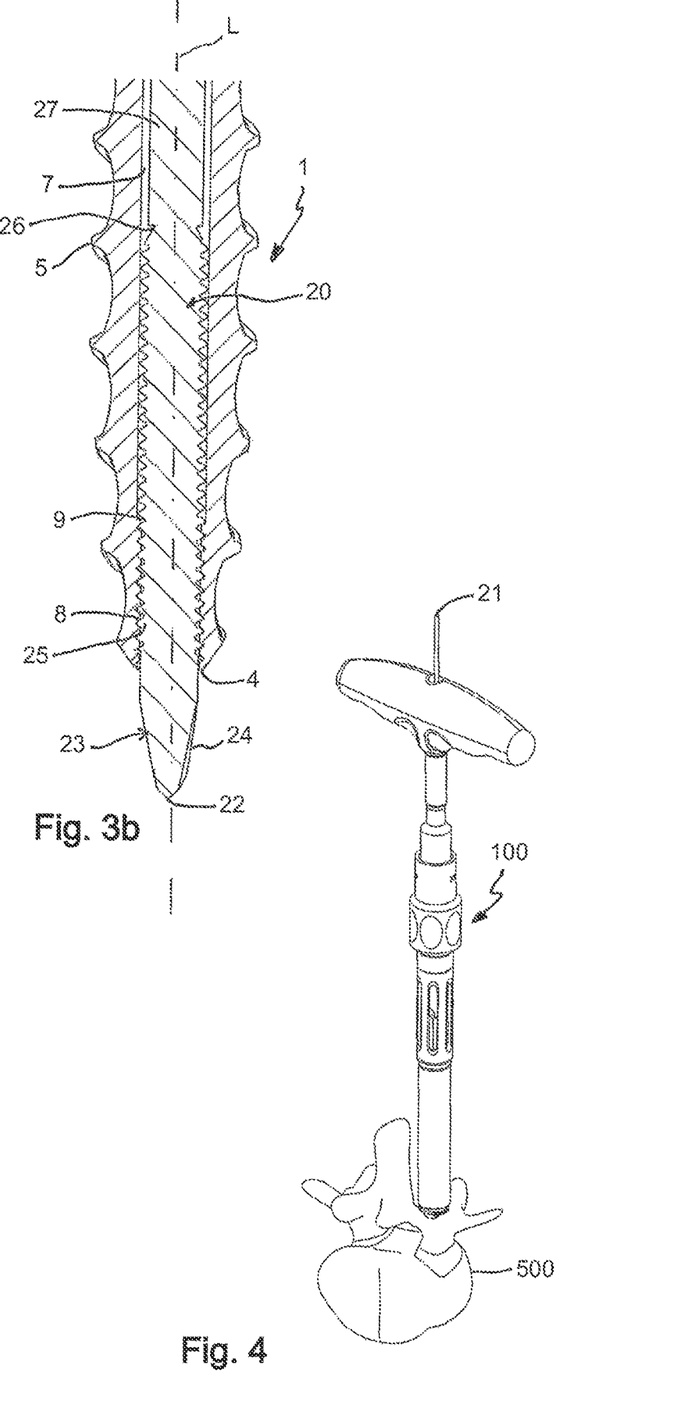

As shown in greater detail in FIGS. 3a and 3b, the bone anchor 1 is cannulated. It includes a channel 7 extending fully through the bone anchor from the head 3 to the second end 4. The channel 7 is formed by a coaxial bore extending from the first end to a distance from the second end 4. The bore axis defines a longitudinal axis L of the channel. In a portion adjacent to the second end 4, the diameter of the channel 7 is slightly smaller than that of the coaxial bore. An internal advancement structure in the form of an internal thread 8 is provided within the channel adjacent to or close to the second end 4. Between the coaxial bore and the advancement structure a shoulder 9 may be formed. The shoulder 9 functions as an abutment to limit the insertion of an elongate instrument. This facilitates achieving an exact positional relationship between the bone anchor 1 and the elongate instrument. A smallest inner diameter of the channel 7 in the bone anchor 1 is defined by the internal thread 8.

Figure 6:
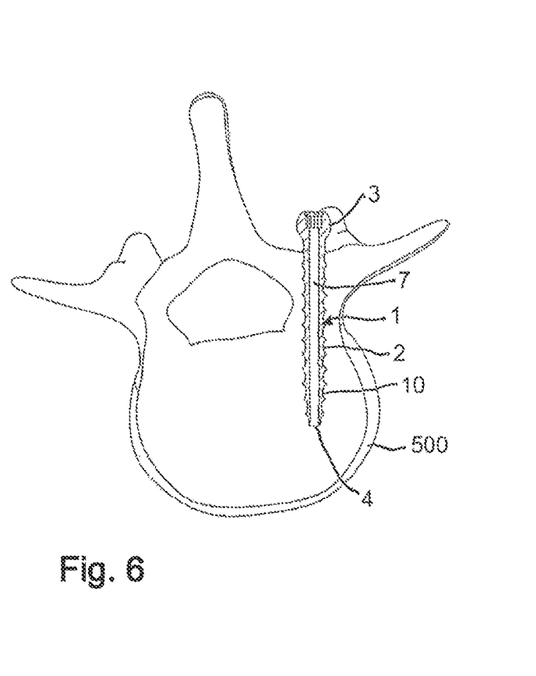
FIG. 6 shows a cross-sectional view of the inserted bone anchor after removal of the elongate instrument.

In the wall of the shank 2, at least one, and preferably a plurality of radial openings 10, shown in FIG. 6, may be provided for the purpose of forming outlets for bone cement or a pharmaceutical substance to be introduced into the bone anchor 1.

The elongate instrument, for example, in the form of the cutting device 20 is a substantially rod-shaped member that has a first end or rear end 21 (shown in FIG. 4) and an opposite second or front end 22. Basically, the cutting device 20 is formed as a cylindrical rod having a length from the rear end 21 to the front end 22 that is greater than the length of the bone anchor 1. Specifically, the length of the cutting device 20 is such that the cutting device 20 is configured to extend through the passage 7 of the bone anchor 1 and project out of the second end 4 of the bone anchor 1 on one side and is configured to extend through an instrument 100 (shown in FIG. 4) for inserting the bone anchor, such that the rear end 21 projects out of the instrument 100.

Adjacent to the front end 22, a tip portion 23 is provided that includes a cutting edge 24. For example, the cutting edge 24 may be formed by a recess in the outer surface of the tip portion 23, wherein at least one edge of the recess is configured to perform a cutting function. Although one cutting edge 24 is shown in the figures, a plurality of cutting edges may be provided. The shape of the cutting edge or the cutting edges, respectively, may be straight, and the cutting edge 24 may extend in a longitudinal direction, or may be helical, or may have any other shape that is configured to cut bone. Adjacent to or at a distance from the tip portion 23, the cutting device 20 includes a section with an external advancement structure in the form of an external thread 25 that is configured to cooperate with the internal thread 8 of the bone anchor 1. The axial length of the section with the external thread 25 may be greater than or equal to the length of the section with the internal thread 8 of the bone anchor 1, so that when the cutting device 20 is inserted in the passage 7 of the bone anchor 1, the position of the cutting device 20 can be precisely adjusted over a certain range. Following the section with the external thread 25, a small neck portion 26 may be provided. The remainder or main portion 27 of the cutting device can be formed as a cylindrical rod with a smooth surface, an outer diameter of which is slightly smaller than an inner diameter of the coaxial bore of the passage 7, so that the cutting device 20 can slide within the coaxial bore.

Moreover, the cutting device 20 may have an engagement structure (not shown) at a position on the main portion 27 that is located outside from the bone anchor 1 when the cutting device is inserted into the channel 7 for engagement with a portion of the instrument 100. Such an engagement structure can be, for example, for rotationally fixing the cutting device 20 relative to the bone anchor 1 when the cutting device 20 has been inserted into the bone anchor and the tip portion 23 extends out of the second end 4 of the bone anchor 1.

The bone anchor 1 and the cutting device 20 may each be made of a bio-compatible material, for example, of titanium or stainless steel, of a bio-compatible alloy, such as NiTi-alloys, for example Nitinol, of magnesium or magnesium alloys, or of a bio-compatible plastic material, such as, for example, polyether ether ketone (PEEK) or poly-l-lactide acid (PLLA). In addition, the parts can be made of the same or of different materials from one another.

For assembly, the bone anchor 1 may be held by the instrument 100, and the cutting device 20 is inserted into the channel 7 of the bone anchor 1 in such a manner that by means of the cooperating threads 8, 25, the length of the cutting device, respectively the cutting portion 23, that protrudes out of the second end 4 of the bone anchor 1 is adjusted. It shall be noted that the cutting device 20 and the bone anchor 1 could also be pre-assembled and then gripped with an instrument. By selecting the type of cutting device 20, for example, in terms of the shape of the cutting edge 24 and the length of the tip portion 23, and by adjusting the length of the portion protruding out from the second end 4 of the bone anchor 1 with the threads, it is possible to provide a system adapted to a specific requirement at the implantation site. Finally, the cutting device 20 is axially fixed to the bone anchor by means of the threads 8, 25, and rotationally fixed through the cooperating engagement portions (not shown) of the cutting device 20 and the instrument 100. Hence, the bone anchor 1 and the cutting device 20 are configured to be inserted as a unit into the bone.

Figure 5A:
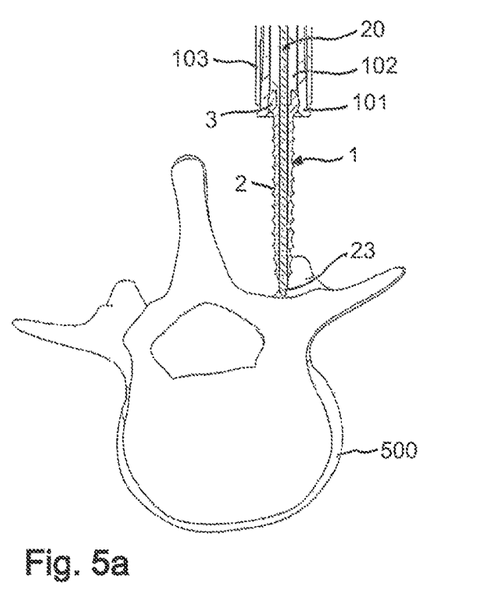
FIGS. 5a to 5c show cross-sectional views of inserting the system of FIGS. 1 to 3b into the pedicle of the vertebra.
Figure 5B:
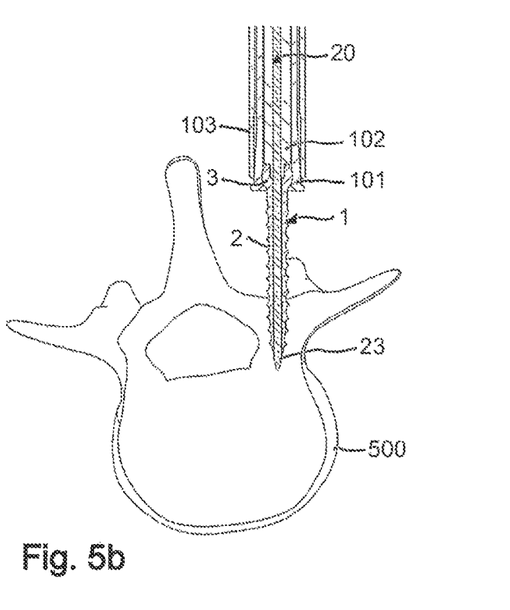
Figure 5C:
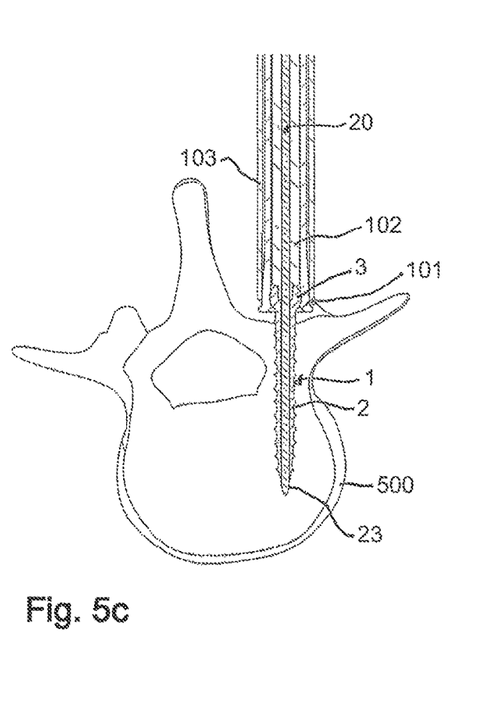

Turning now to FIGS. 5a to 5c, the bone anchor 1 with the cutting device 20 and a portion of the instrument 100 is shown. The instrument 100 is shown as an exemplary embodiment, and includes a first head engagement portion 101 that engages the head 3 from the outside thereof, a second head engagement portion 102 that engages the head 3 in the recess 6, and a clamping sleeve 103 that presses the first head engagement portion 101 towards the head 3 so that the head 3 of the bone anchor 1 is firmly clamped in the instrument. The second head engagement portion 102 has a passage for passing through the cutting device 20. As shown in FIG. 5a, the unit including the bone anchor 1 and cutting device 20, is placed at a position where the bone anchor 1 is to be inserted, for example, a pedicle of a vertebra 500. The cutting edge 24 is used for penetrating cortical bone. Hence, the tip portion 23 prepares the pathway for the bone anchor 1, so that the bone anchor 1 can be easily screwed in. Pre-drilling of a hole can be omitted.

Then, as shown in FIGS. 5b and 5c, the bone anchor 1 is screwed into the pedicle until the shank 2 is finally implanted and the head 3 projects out of the bone surface. The placement of the bone anchor 1 with the cutting device 20 may be carried out with the assistance of an imaging method.

When the bone anchor is in the final position, the cutting device 20 is screwed back and removed from the bone anchor, as shown in FIG. 6. If necessary, the second end 4 can be closed by inserting a plug member and/or bone cement, or another substance can be injected which may flow out of the openings 10.

Figure 7:
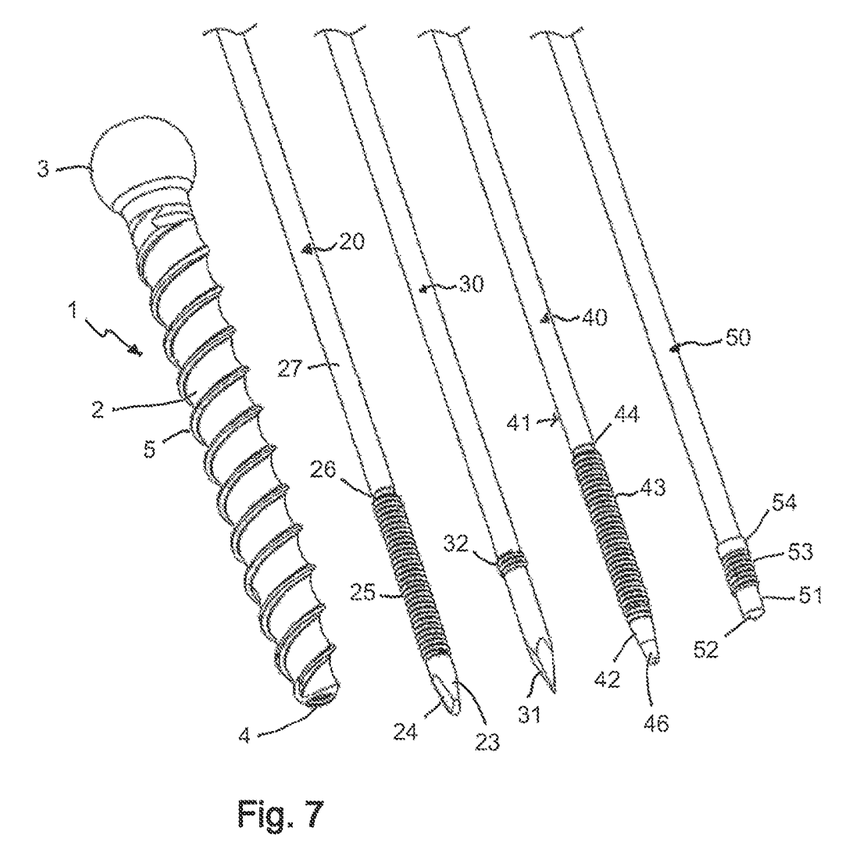
FIG. 7 shows a perspective view of the bone anchor and various elongate instruments that each can be used with the bone anchor to form a system.

FIG. 7 depicts the bone anchor 1 and various elongate instruments. Such instruments may include, for example, the cutting device 20, a medical guide wire 30, such as a modified K-wire, a sensor 40, and a marker 50. Each of the instruments together with the bone anchor 1 forms a unit. The various instruments and the bone anchor may form a modular system that permits selectively combining one elongate instrument with the bone anchor 1, depending on the intended use.

Figure 8:
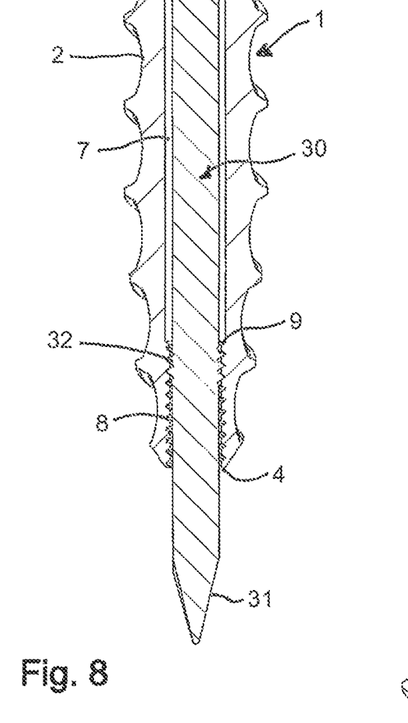
FIG. 8 shows a cross-sectional view of a portion of the system, with the elongate instrument including a modified K-wire.

The elongate instrument in the form of a medical guide wire 30, such as a modified K-wire, is shown in greater detail in FIG. 8. The guide wire 30 has a substantially smooth outer surface with an outer diameter slightly smaller than an inner diameter of the thread 8, so that the guide wire 30 can be guided through the channel 7 of the bone anchor 1. As usual, the guide wire 30 has a tip portion 31 that is configured to be pressed into bone. At a distance from the tip portion 31, an external advancement structure in the form of an external thread 32 is provided that is configured to cooperate with the internal thread 8 of the bone anchor 1. Preferably, an axial length of the external thread 32 is smaller than an axial length of the internal thread 8. More specifically, the axial length of the external thread 32 includes only as many thread turns as are necessary to axially secure the guide wire 30 against sliding in the channel 7. This may be at least one or only a small number of thread turns. The external thread 32 may be located at a position away from the tip portion 31, such that the tip portion 31, and preferably a portion 33 adjacent to the tip portion 31, projects out of the second end 4 when the external thread 32 engages the internal thread 8.

In use, the guide wire 30 and the bone anchor 1 are assembled by screwing the guide wire 30 into the bone anchor 1 and the system is placed as a unit onto the bone surface so that the tip portion 31 of the guide wire is pressed into the bone. Thereafter, the bone anchor 1 can be screwed down until the threads are out of engagement. In this condition, the guide wire can be used as a typical guide wire and the bone anchor 1 and other parts may be guided along the guide wire towards the implantation site. Or, the bone anchor and the modified K-wire can be placed as a unit onto the bone surface, the K-wire can be pressed into the bone and screwed further down along the internal thread.

Figure 9:
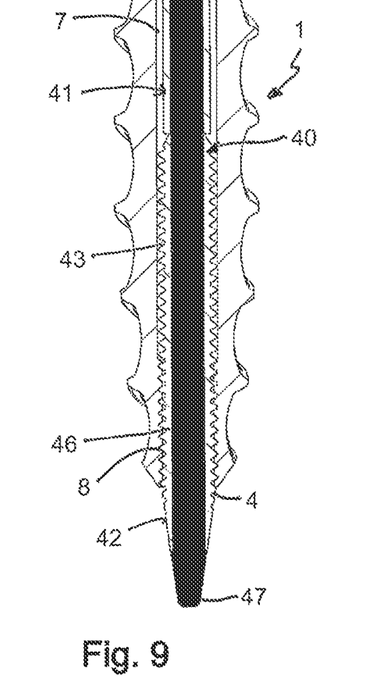
FIG. 9 shows a cross-sectional view of a portion of the system, with the elongate instrument including a sensor.

The elongate instrument in the form of a sensor 40 is shown in FIG. 9. As shown in FIG. 9, the sensor 40 includes a housing 41 which is substantially tube-shaped and that is configured to be passed through the channel 7 of the bone anchor 1. The housing 41 has a tip portion 42 that may extend through the second end 4. Adjacent to the tip portion 42, the housing 41 includes an advancement structure in the form of an external thread 43 that is configured to cooperate with the internal thread 8 of the bone anchor 1. The axial length of the external thread 43 may be greater than or equal to the axial length of the internal thread 8. Adjacent to the external thread 43, a neck portion 44 may be present that is followed by a main portion 45 of the housing 41 with a smooth outer surface. A sensor element 46 is positioned in the housing 41, wherein the sensor element 46 includes a tip portion 47 that is configured to sense respective characteristics, such as, for example, a density of the bone, or which is configured to perform neuro-monitoring. Any other suitable sensor element may be conceivable.

The sensor 40 may be inserted when the bone anchor has already been inserted into the bone, or may be preassembled with the bone anchor 1 and inserted together with the bone anchor 1 into the bone.

Figure 10:
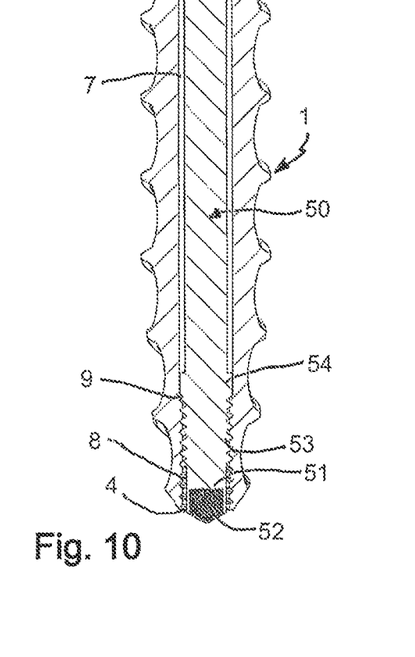
FIG. 10 shows a cross-sectional view of a portion of the system, with the elongate instrument including a marker.

An elongate instrument in the form of a marker 50, such as a marker for detection through X-rays and/or marking a location on the bone, is shown in greater detail in FIG. 10. The marker 50 is substantially rod-shaped with an inner diameter that is slightly smaller than the inner diameter of the coaxial bore of the bone anchor 1. A tip portion 51 is provided which includes a marker element 52, for example an X-ray detectable element. At a distance from the tip portion 51, an external advancement structure in the form of an external thread 53 is provided that is configured to cooperate with the internal thread 8 of the bone anchor 1. The axial length of the external thread 53 may be smaller or equal to the axial length of the internal thread 8. A shoulder 54 that may be adjacent to the external thread 53 is configured to abut against the shoulder or step 9 in the channel 7 to limit the insertion of the marker 50 into the bone anchor. The shoulder 54 is located at such a position that when the shoulder 54 abuts against the shoulder 9, the marker element is positioned at the second end 4 and may slightly project out of the second end 4. By means of the stop provided by the shoulder 9, a fully inserted position of the marker 50 relative to the bone anchor 1 is defined. Therefore, the marker 50 can precisely indicate the position of the bone anchor 1.

In use, preferably the marker 50 and the bone anchor 1 may be preassembled and inserted into the bone.

Further modifications of the above-described system may also be conceivable. The shape of the bone anchor is not restricted to the shape shown in the embodiment. Any kind of bone anchor may be used, such as, for example, bone anchors without a bone thread, such as bone nails. The head of the bone anchor is shown to be spherically-shaped. However, any other suitable head may also be conceivable. In particular, receiving parts for providing a polyaxial bone anchor may be attached to the head.

The channel of the bone anchor can have a shape other than cylindrical. The openings in the wall of the bone anchor can have any shape, in particular a longitudinally extending slit is also conceivable. Finally, the openings can be omitted.

The advancement structure is shown to be a thread, however, a plurality of concentric ribs to form an advancement structure or another advancement structure that permits continuously or incrementally advancing the cutting device within the channel may be used.

The various features of the elongate instruments may also be combined to provide other embodiments of elongate instruments.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:
1. A bone anchor comprising:
a shank having a first end, a second end opposite the first end, and an inner wall defining an annular region at the first end that forms a closed ring, an annular region at the second end that forms another closed ring, and a channel that extends entirely through the shank from the first end to the second end along a channel axis;
wherein an internal advancement structure provided on the inner wall is configured to cooperate with an external advancement structure of an instrument that is positionable in the channel, wherein at least part of the internal advancement structure is positioned axially between the second end and the annular region at the first end; and wherein a majority of an entire length of the inner wall that extends from the first end to the second end is formed to be free of any internal advancement structures, and wherein a first portion of the internal advancement structure that is positioned closest to the second end comprises a projection that extends as far radially into the channel as any portion of the inner wall located axially between the first portion and the first end so as to be engageable with an instrument that is inserted into the channel from the first end.

2. The bone anchor of claim 1, wherein at least part of the internal advancement structure is positioned closer axially to the second end than to the first end.

3. The bone anchor of claim 1, wherein the internal advancement structure comprises an internal thread.

4. The bone anchor of claim 3, wherein the internal thread is a cylindrical thread.

5. The bone anchor of claim 1, wherein a stop is provided at the inner wall of the shank to limit axial movement of an instrument that is inserted into the channel.

6. The bone anchor of claim 1, further comprising a head at the first end of the shank, and wherein an outer width of the head is greater than an outer width of the first end of the shank.

7. The bone anchor of claim 6, wherein the head is spherical segment-shaped.

8. The bone anchor of claim 1, wherein the internal advancement structure is adjacent to the second end of the shank.

9. The bone anchor of claim 1, wherein the entire internal advancement structure is closer to the second end of the shank than to the first end of the shank.

10. A bone anchor comprising:
a shank having a first end, a second end opposite the first end, and an inner wall defining an annular region at the second end that forms a closed ring and a channel that extends entirely through the shank from the first end to the second end along a channel axis;
wherein an internal thread provided on the inner wall is configured to cooperate with an external thread of an instrument that is positionable in the channel; and
wherein a majority of an entire length of the inner wall that extends from the first end to the second end is unthreaded, and wherein a first portion of the internal thread that is positioned closest to the second end extends as far radially into the channel as any portion of the inner wall located axially between the first portion and the first end so as to be engageable with an instrument that is inserted into the channel from the first end.

11. The bone anchor of claim 10, wherein at least part of the internal thread is positioned axially between the second end and the annular region at the first end.

12. The bone anchor of claim 10, wherein at least part of the internal thread is positioned closer axially to the second end than to the first end.

13. The bone anchor of claim 10, wherein the internal thread is a cylindrical thread.

14. The bone anchor of claim 10, wherein a stop is provided at the inner wall of the shank to limit axial movement of an instrument that is inserted into the channel.

15. The bone anchor of claim 10, wherein the internal advancement structure is adjacent to the second end of the shank.

16. The bone anchor of claim 10, further comprising a head at the first end of the shank, and wherein an outer width of the head is greater than an outer width of the first end of the shank.

17. The bone anchor of claim 16, wherein the head is spherical segment-shaped.

18. The bone anchor of claim 10, wherein the entire internal thread is closer to the second end of the shank than to the first end of the shank.

19. A system comprising:
a bone anchor comprising a shank having a first end, a second end opposite the first end, and an inner wall defining a channel that extends entirely through the shank from the first end to the second end along a channel axis, wherein an internal advancement structure is provided on the inner wall;
a non-implantable first instrument configured to extend through the channel to a position closer axially to the second end of the shank than to the first end of the shank, the first instrument comprising an external advancement structure configured to cooperate with the internal advancement structure of the bone anchor to hold an axial position of the first instrument relative to the bone anchor; and
a non-implantable second instrument different from the first instrument that is configured to extend through the channel to a position closer axially to the second end of the shank than to the first end of the shank, the second instrument comprising an external advancement structure configured to cooperate with the internal advancement structure of the bone anchor to hold an axial position of the second instrument relative to the bone anchor;
wherein the internal advancement structure is interchangeably engageable with the external advancement structures of the first and second instruments.

20. The system of claim 19, wherein the external advancement structure of the first instrument and the external advancement structure of the second instrument are different from one another.

* * * * *